(12) United States Patent
Berry et al.

(10) Patent No.: US 12,064,321 B2
(45) Date of Patent: *Aug. 20, 2024

(54) KINESIOLOGY SUPPORT TAPE

(71) Applicants: Levi Berry, Mapleton, UT (US); Christine Berry, Mapleton, UT (US)

(72) Inventors: Levi Berry, Mapleton, UT (US); Christine Berry, Mapleton, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/688,884

(22) Filed: Mar. 7, 2022

(65) Prior Publication Data

US 2022/0257425 A1    Aug. 18, 2022

Related U.S. Application Data

(63) Continuation of application No. 17/006,551, filed on Aug. 28, 2020, now Pat. No. 11,266,540.
(Continued)

(51) Int. Cl.
*A61F 13/06* (2006.01)

(52) U.S. Cl.
CPC .................................. *A61F 13/067* (2013.01)

(58) Field of Classification Search
CPC .. A61F 5/00; A61F 5/01; A61F 5/0585; A61F 5/0113; A61F 5/14; A61F 5/0111; A61F 5/0127; A61F 13/067; A61F 13/0246; A61F 13/0253; A61F 13/064; A61F 13/06; A61F 13/0273; A61F 13/0259; A61F 13/023; A61F 13/02; A61F 13/00; A61F 13/00021; A61F 13/00089; A61F 13/00361; A61F 2013/00582; A61F 2013/00246; A61F 2013/00251; A61F 2013/00255; A43B 5/0437; A43B 7/00; A43B 7/14; A43B 7/141; A43B 7/1415; A43B 7/142

USPC ....... 36/140, 145, 88, 91, 43; 623/29; 602/1, 602/5, 6, 23, 28, 29, 41, 52, 54, 57, 58, 602/59, 60–62; 128/882

See application file for complete search history.

(56) References Cited

U.S. PATENT DOCUMENTS

| | | |
|---|---|---|
| 4,744,355 A | 5/1988 | Faasse, Jr. |
| 5,861,348 A | 1/1999 | Kase |

(Continued)

FOREIGN PATENT DOCUMENTS

| | | | | |
|---|---|---|---|---|
| DE | 102011014736 A1 | * | 9/2012 | ............. A43B 17/00 |
| WO | WO-2007001664 A2 | * | 1/2007 | ............. A43B 7/142 |
| WO | WO 2007001664 A2 | | 1/2007 | |

OTHER PUBLICATIONS

Machine translation of DE 102011014736 A1 (Year: 2012).*

(Continued)

*Primary Examiner* — Caitlin A Carreiro
(74) *Attorney, Agent, or Firm* — Young Basile Hanlon & MacFarlane, P.C.

(57) ABSTRACT

In one embodiment, an anatomical support device includes an elongate body. The elongate body includes a first portion extending along a longitudinal axis between a first end and an oppositely positioned second end, a first wing extending transversely from the first portion, and a second wing extending transversely from the first portion. An adhesive material is positioned on at least a portion of one side of the elongate body. The elongate body is rigid in a first direction extending in-line with the longitudinal axis and is stretchable in a second direction extending transversely to the longitudinal axis.

10 Claims, 10 Drawing Sheets

Related U.S. Application Data

(60) Provisional application No. 63/016,426, filed on Apr. 28, 2020.

(56) References Cited

U.S. PATENT DOCUMENTS

| | | | |
|---|---|---|---|
| 9,308,115 B2 | | 4/2016 | Quinn |
| 11,266,540 B2 * | | 3/2022 | Berry ................ A61F 13/067 |
| 2005/0240139 A1 * | | 10/2005 | Bushby ................ A61B 50/00 |
| | | | 602/61 |
| 2010/0312160 A1 * | | 12/2010 | Creighton ............. A61L 15/58 |
| | | | 602/62 |
| 2014/0245700 A1 * | | 9/2014 | Bushby ................ A43B 7/226 |
| | | | 83/13 |
| 2014/0276319 A1 | | 9/2014 | Ibrahim et al. |
| 2016/0106595 A1 | | 4/2016 | Arbesman et al. |
| 2016/0262943 A1 | | 9/2016 | Arbesman et al. |
| 2016/0354224 A1 * | | 12/2016 | Bushby ................ A61F 5/0111 |
| 2017/0049602 A1 * | | 2/2017 | Kuehl ................ A61F 13/0273 |
| 2018/0235827 A1 | | 8/2018 | Rich et al. |
| 2018/0333315 A1 | | 11/2018 | Singh |
| 2019/0298562 A1 * | | 10/2019 | Bushby ................ B32B 3/266 |
| 2019/0328580 A1 * | | 10/2019 | Emslander .......... A61F 13/0259 |

OTHER PUBLICATIONS

Brisbane Podiatrist demonstrates Plantar Facsiitis Strapping technique—'Low Dye', Shoes Feet Gear—Brisbane Podiatry, https://www.youtube.com/watch?v=pwE5i43CEdk, published May 14, 2014, pp. 1-6.

Plantar Fasciitis Taping Technique, Sports Injury Physio, https://www.youtube.com/watch?v=2oJEE26YpLQ, published Nov. 12, 2016, pp. 1-11.

Laura Verbruggen, Melissa Thompson, Chris Durall, The Effectiveness of Low-Dye Taping in Reducing Pain Associated with Plantar Fasciitis, Journal of Sport Rehabilitation, 2018, pp. 94-98vol. 27 No. 1, DOI: https://doi.org/10.1123/jsr.2016-0030, Sep. 2016.

* cited by examiner

KINESIOLOGY SUPPORT TAPE

CROSS-REFERENCE TO RELATED APPLICATIONS

This application is a continuation of U.S. patent application Ser. No. 17/006,551 filed Aug. 28, 2020 (now U.S. Pat. No. 11,266,540), which claims the benefit of U.S. Patent App. Ser. No. 63/016,426 filed Apr. 28, 2020, both of which are hereby incorporated by reference.

FIELD

The present disclosure generally relates to anatomical support devices configured to provide support at one or more anatomical locations. More particularly, but not exclusively, the present disclosure relates to an anatomical support device in the form of a partially stretchable material including an adhesive configured for adhering the device to an anatomical location.

BACKGROUND

Unless otherwise indicated herein, the materials described herein are not prior art to the claims in the present application and are not admitted to be prior art by inclusion in this section.

A number of physical ailments may cause pain, including potentially significant pain, when a person undertakes various activities. Some physical ailments may also cause pain lasting beyond the time when the activities are undertaken. For example, plantar proximal heel pain commonly referred to as plantar fasciitis is a common foot ailment that causes significant pain to a person during activities that include simply walking. Plantar fasciitis affects millions of people every year, and people in their 4th to 6th decade have a significantly higher incidence of plantar fasciitis. People affected by plantar fasciitis may be active or sedentary, and it is a common injury associated with running. In the United States, it has been reported that over 2 million patients are treated in an outpatient setting every year for acute plantar fasciitis. Plantar heel pain is also reported to be the most common lower extremity pathology encountered by foot and ankle surgeons with around 11-15% of adult patients seeking medical attention from a podiatric physician will present with a chief complaint of heel pain.

Some common treatment options for plantar fasciitis and other physical ailments may include injections, resting, orthotics, stretching, physical therapy, bandaging/taping and/or even surgery. With some treatments, a significant amount of time may pass before results may become apparent. Some temporary treatments for plantar fasciitis and other physical ailments may be employed to help an injured person with pain and recovery but their application and removal are often tedious. In addition, temporary treatments may limit mobility and they often consume excessive amounts of materials.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

In one embodiment, an anatomical support device includes an elongate body including a first portion extending along a longitudinal axis between a first end and an oppositely positioned second end, a first wing extending transversely from the first portion, and a second wing extending transversely from the first portion. An adhesive material is positioned on at least a portion of one side of the elongate body. The elongate body is rigid in a first direction extending in-line with the longitudinal axis and is stretchable in a second direction extending transversely to the longitudinal axis.

In another embodiment, a method for treating plantar fasciitis includes providing an anatomical support device. The anatomical support device includes an elongate body including a first portion extending along a longitudinal axis between a first end and an oppositely positioned second end, a first wing extending transversely from the first portion, and a second wing extending transversely from the first portion. An adhesive material is positioned on at least a portion of one side of the elongate body. The elongate body is rigid in a first direction extending in-line with the longitudinal axis and is stretchable in a second direction extending transversely to the longitudinal axis. The method also includes applying the device to the bottom of a human foot including a number of toes, a heel, a malleolus, and an extensor retinaculum. The first end is positioned toward the toes, the second end is positioned toward the heel, the first wing is stretched in a direction of the malleolus, and the second wing is stretched in a direction of the extensor retinaculum.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Reference will now be made to the drawings to describe various aspects of example embodiments of the invention. It is to be understood that the drawings are diagrammatic and schematic representations of such example embodiments, and are not limiting of the present invention, nor are they necessarily drawn to scale.

The present disclosure generally relates to anatomical support devices configured to provide support for one or more anatomical locations. More particularly, but not exclusively, the present disclosure relates to an anatomical support device in the form of a partially stretchable material including an adhesive configured for adhering the device to an anatomical location. Although various embodiments may be described in the context of use at various anatomical locations, embodiments disclosed herein may be employed in other fields or operating environments where the functionality disclosed herein may be useful. Accordingly, the scope of the invention should not be construed to be limited to the example implementations and operating environments disclosed herein.

According to one or more embodiments of the present disclosure, a kinesiology support tape ("support tape") may be configured and used in a particular manner to provide support to various anatomical locations and/or treat ailments. In one form, the support tape disclosed herein may be used to support or treat ailments such as plantar fasciitis, although a number of other uses are also possible as will be discussed in greater detail below. As a corollary, the size and/or shape of the support tape may be configured and/or modified to provide support for a variety of different anatomical locations for supporting and/or treating ailments of the same.

Figure 1:
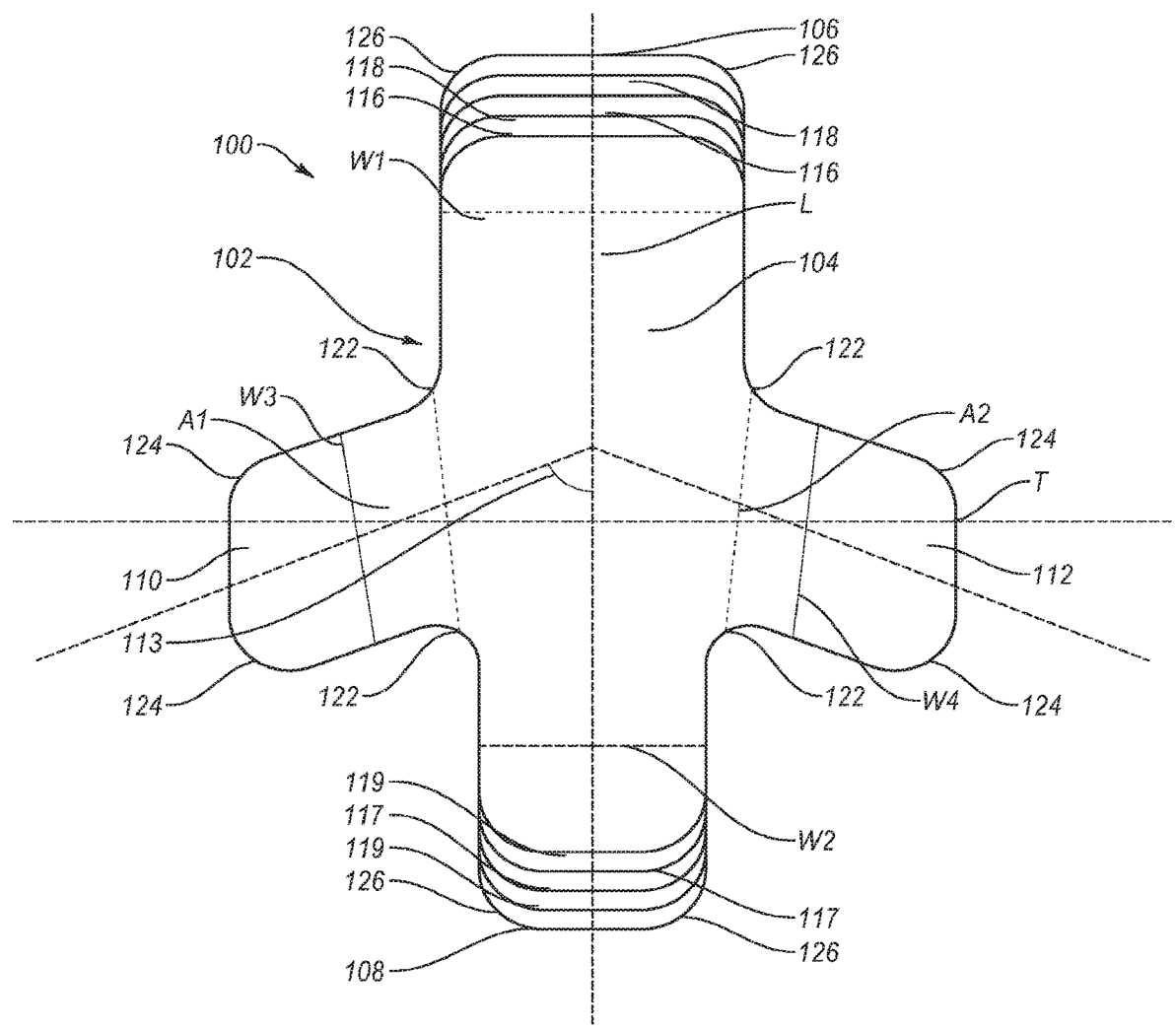
FIG. 1 illustrates an example configuration of a kinesiology support tape, according to at least one embodiment of the present disclosure.
Figure 2B:
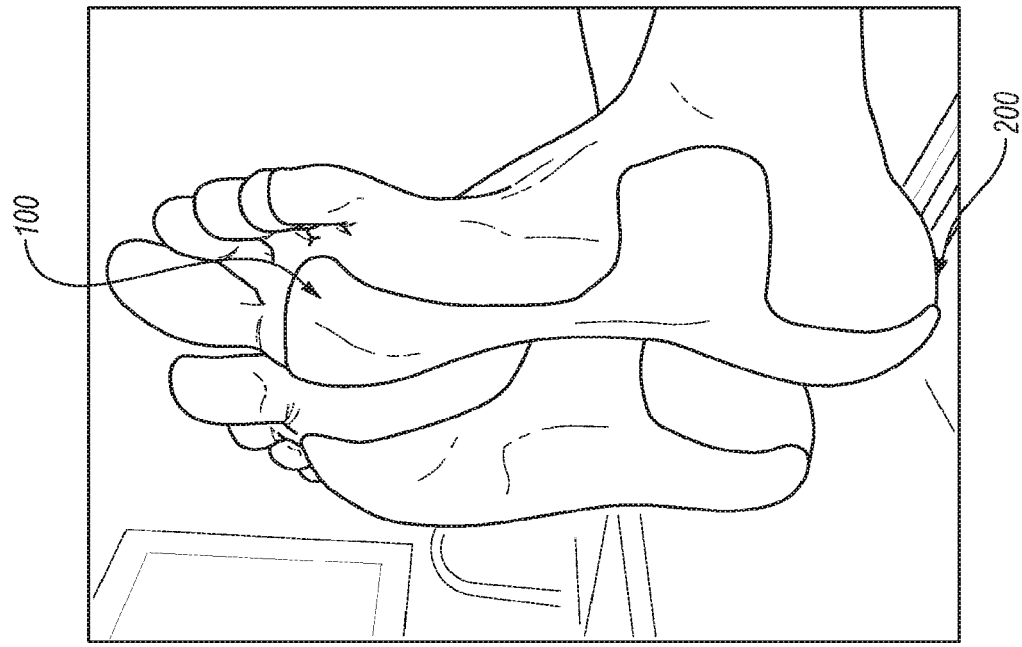
FIGS. 2A-D illustrate an example use of the support tape of FIG. 1 for treatment of plantar fasciitis.
Figure 2A:
Figure 2D:
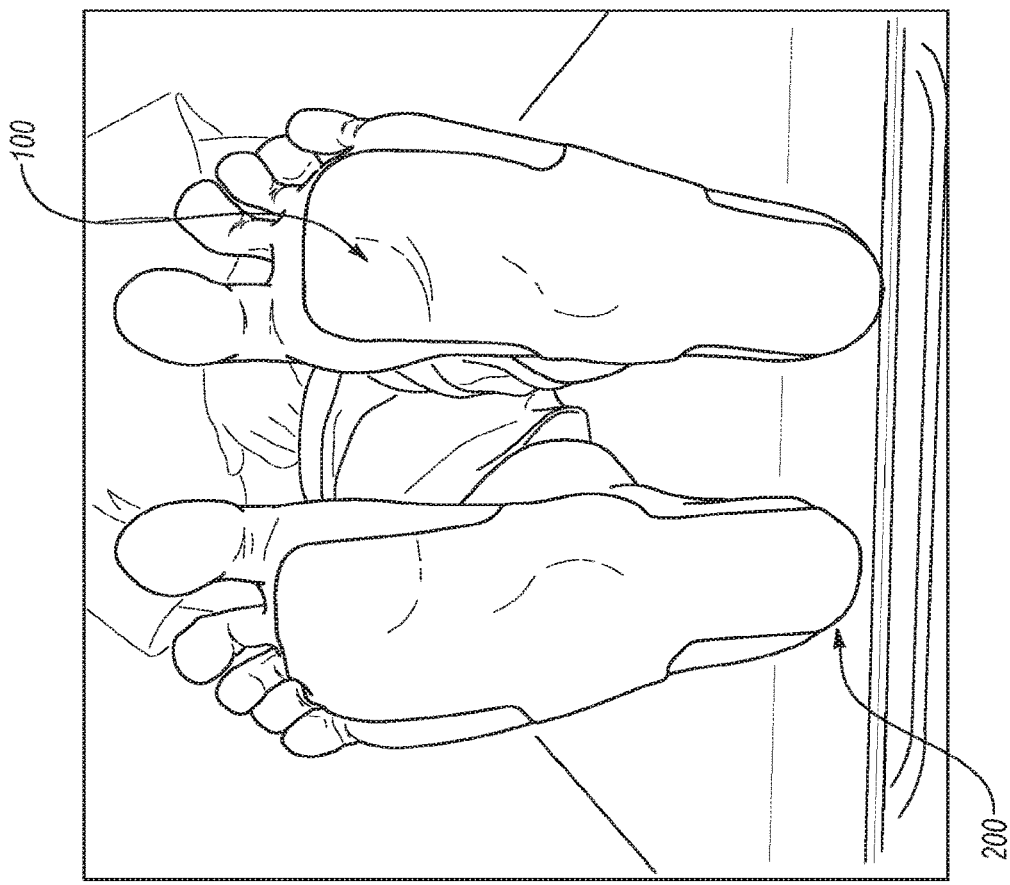
Figure 2C:

With reference to FIG. 1 for example, a support tape 100 includes a body 102 having a main or first portion 104 which extends along a longitudinal axis L between a first end 106 and an opposite, second end 108. The body 102 also includes a first flap or wing 110 which extends transversely from the first portion 104 in a first direction, and a second flap or wing 112 which extends transversely from the first portion 104 in a second direction, opposite of the first direction. The first and second wings 110, 112 may be integrally formed with the first portion 104 of the body 102, although forms in which the first and second wings 110, 112 are separate components added to the first portion 104 of the body 102 are also contemplated. In the illustrated form, the first and second wings 110, 112 generally extend obliquely to the longitudinal axis L along axes A1 and A2, respectively. Axes A1 and A2, as well as the first and second wings 110, 112, in turn also extend obliquely to a transverse axis T which extends orthogonally to the longitudinal axis L. The axes A1 and A2 may intersect the longitudinal axis L and form an angle 113 which may be in the range of about 60 to about 80 degrees, about 65 to about 75 degrees, or about 70 degrees. However, other variations in this angle and the positioning of the first and second wings 110, 112 relative to the longitudinal axis L are also possible.

The body 102 may include a length between the first end 106 and the second end 108 which is suitable for a particular application at an anatomical location. In one form for example when the support tape 100 is configured for use in treating plantar fasciitis, the body 102 may include a length which generally corresponds to the length of a foot to which it may be applied. In order to accommodate feet of various sizes, and/or other anatomical locations of different sizes, a number of different sizes of the support tape 100 could be provided and then the most suitable size could be selected for a given application.

Alternatively, the support tape 100 could include a number of perforations 116 (only a few of which have been identified to preserve clarity) located near the first end 106 and a number of perforations 117 (only a few of which have been identified to preserve clarity) located near the second end 108. The perforations 116, 117 may facilitate customizing the length of the body 102 such that a single support tape 100 could be provided and customized for a number of different applications. More specifically, in order to adjust the size of the support tape 100, one or more sections 118 (only a few of which have been identified to preserve clarity) located near the first end 106 of the body 102 and/or one or more sections 119 (only a few of which have been identified to preserve clarity) located near the second end 108 of the body 102 may be torn away or removed from the body 102 to provide it with a desired length for a particular application. In one form for example, removal of one section 118 and one section 119 may provide the body 102 with a length that corresponds to a smaller size or range of sizes of a human foot, although other variations are possible.

While not illustrated, it is also possible that one or both of the first and second wings 110, 112 could also include a number of perforations to facilitate customization of the size of one or both of the first and second wings 110, 112. For example, a section of one or both of the first and second wings 110, 112 could be removed to accommodate use of the support tape 100 with a number of different sized anatomical features.

In the illustrated form, the body 102 of the support tape 100 includes a first width W1 along a section thereof positioned between the first and second wings 110, 112 and the first end 106. The body 102 of the support tape 100 also includes a second width W2 along a section thereof positioned between the first and second wings 110, 112 and the second end 108. The first width W1 is greater than the second width W2 in the illustrated form, although forms where the first width W1 is smaller than the second width W2 or the first width W1 and the second width W2 are the same are also possible. In one particular but non-limiting form, the width W1 may be in the range of about 4 to about 10 cm, about 5 to about 9 cm, about 6 to about 8 cm or about 7 cm, just to provide a few possibilities, while the width W2 may be in the range of about 2 to about 8 cm, about 3 to about 7 cm, about 4 to about 6 cm, or about 5 cm, just to provide a few possibilities, The first wing 110 includes a width W3 and the second wing 112 includes a width W4. In the illustrated form, the widths W3 and W4 are the same, although forms where the widths W3 and W4 are different are also possible. In addition, the widths W3 and W4 are less than the width W1 but slightly greater than the width W2 in the illustrated form. Again, it should be appreciated that the relative sizing between the widths W1-W4 may vary as one or more of the widths W1-W4 changes. In addition, the distance between the longitudinal axis L and the lateral edges of the first and seconds winds 10, 12 (e.g., along a long dimension of the first and second wings 10, 12) may be greater than the widths W3 and W4.

While not previously mentioned, it should be appreciated that the body 102 may include a number of rounded corners or transitions along its periphery. By way of example, a number of concave arcuate transitions 122 are positioned or extend between the first portion 104 of the body 102 and the first and second wings 110, 112. Moreover, the first and second wings 110, 112 include a number of convex arcuate transitions or corners 124 positioned on the ends thereof while the first portion 104 of the body 102 includes a number of convex arcuate transitions or corners 126 positioned on the ends 106, 108 thereof. The rounded corners or transitions of the body 102 may, for example, promote or assist in flat positioning of the support tape 100 relative to an anatomical location having a complex geometry where different portions of the support tape 100 are located in different planes etc. from one another.

The support tape 100 may be formed of a flexible, semi-flexible, or rigid material which includes an adhesive or adhesive material on at least a portion of one side thereof. In some forms for examples, the support tape 100 may include a number of different portions where some are flexible, some are semi-flexible, and/or some are rigid. In one particular but non-limiting form, the support tape 100 may have elastic properties which facilitate stretching of the tape. In one aspect, the elastic properties may allow the support tape 100 to be stretched in one direction but not another. For example, in one form, the support tape 100 may be stretched in a direction extending along, or substantially along, the transverse axis T while the support tape 100 may be rigid or may not be stretched in a direction extending along, or substantially along, the longitudinal axis L. In one form, the support tape 100 may be formed of a woven textile material which includes an adhesive material applied to at least a portion thereof and is otherwise configured to impart the flexibility characteristics discussed above.

The support tape 100 may include a backing material (not shown) applied to and covering at least a portion of the adhesive or adhesive material. In one form, the backing material may include a plurality of cooperating pieces or sections configured to cover all or part of the adhesive material. In one aspect, the cooperating pieces of the backing material may overlap with one another. In another aspect, the backing material may include a number of perforations separating the plurality of pieces or sections from one another with the perforations being configured to facilitate individual removal of the cooperating pieces from the adhesive material.

In one form, a first section of the backing material may cover a first section of the first portion 104 of the body 102 extending from the first end 106 toward the second end 108, and a second section of the backing material may cover a second section of the first portion 104 of the body 102 extending from the second end 108 toward the first end 106. The first and second sections of the backing material may overlap with one another or a perforation may be positioned therebetween. In one form, a third section of backing material may be positioned between the first and second sections of the backing material. A fourth section of the backing material may cover the wing 110 and overlap with the first, second and/or third sections of the backing material or a perforation may be positioned between these sections of the backing material. A fifth section of the backing material may cover the wing 112 and overlap with the first, second and/or third sections of the backing material or a perforation may be positioned between these sections of the backing material.

When the backing material is formed from a number of cooperating pieces or sections, the pieces or sections of the backing material may be successively removed as the support tape 100 is applied to an anatomical location. In this arrangement, the support tape 100 may be incrementally applied to the anatomical location without portions thereof adhering to the anatomical location in an undesired position. In a form where the backing material includes four cooperating pieces or sections for example, a first section may be removed to facilitate application of the first end 106 to an anatomical location, followed by removal of a second section to facilitate application of the second end 108 to an anatomical location. Once these sections have been removed and the first portion 104 of the elongate body 102 is applied to the anatomical location, a third section may be removed to facilitate application of the wing 110 to the anatomical location and a fourth section may be removed to facilitate application of the wing 112 to the anatomical location. Of course, other variations in the order in which the sections are removed and the related portions of the support tape 100 applied to the anatomical locations are possible.

As indicated above, the support tape 100 may be used for treating or supporting a number of ailments at a variety of anatomical locations. In one non-limiting use, the support tape 100 may be applied to the underside of a foot 200 to help in treatment of plantar fasciitis as illustrated in FIGS. 2A-2D. For example, the support tape 100 may be applied to a foot 200 with the first end 106 thereof directed toward the toes of the foot 200 and the second end 108 thereof directed toward the heel of the foot 200. In this configuration, the first and second wings 110, 112 may be oriented for application to the sides of the foot 200 and/or ankle. In this arrangement, the first and second wings 110, 112 may provide support in a manner similar to that provided by the PT tendon of the foot 200 and to support the medial arch, and end at an area of the foot 200 where the fascial planes are more stable. Since the support tape 100 may be stretchable along the long dimension of the first and second wings 10, 12 (i.e., in a general direction that is transverse to the longitudinal axis L), the first and second wings 10, 12 may provide dynamic support to the PT tendon and the medial arch. In one form for example, one of the first and second wings 110, 112 may be sized to end (when the support tape 100 is applied to the foot 200) near the anterior aspect of the medial malleolus, overlying the apical insertion of the flexor retinaculum. The other of the first and second wings 110, 112 may be sized to end (when the support tape 100 is applied to the foot) near the stable soft tissue planes at the distal segment of the extensor retinaculum.

In the context of being used to treat plantar fasciitis, the support tape 100 may be inelastic, or non-stretchable along the longitudinal axis L, which may help reduce strain on the plantar fascia. Similarly, since the support tape 100 may be applied with the longitudinal axis L generally extending in-line with the long axis of the foot, the inelastic, or non-stretchable characteristics of the support tape 100 along the longitudinal axis L may provide static support for the long art and plantar fascia of the foot. As indicated above, the support tape 100 may at the same time also be elastic, or stretchable along the transverse axis T (e.g., along the first and second wings 10, 12), which may allow dynamic support of PT tendon and the medial arch to lift the medial arch. Similarly, the support tape 100 may provide both support and flexibility from different directions. In contrast, other support components may not stretch at all of stretch in all directions.

As indicated above, use of the support tape 100 is not limited to treatment of plantar fasciitis. Further, the particular configuration (e.g., size and/or shape) of the support tape 100 illustrated is merely an example and not meant to be limiting. For instance, different configurations of the support tape 100 may have only one wing, or more than two wings. Further, one or more of the angles, locations, widths, lengths, etc. of the wings 110, 112 may vary. Additionally, the width and/or length of the body 102 of the support tape 100 may vary.

Figure 3:
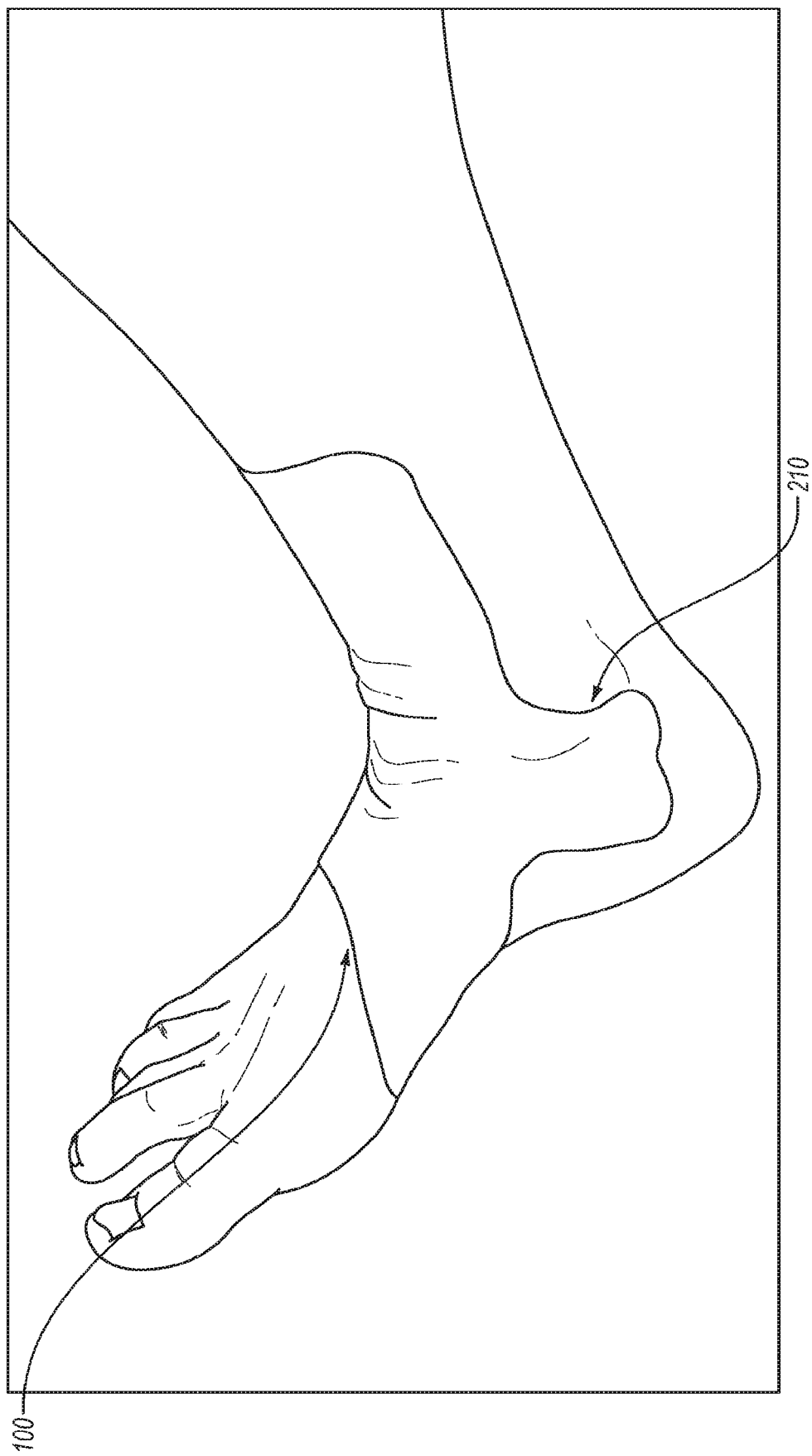
FIG. 3 illustrates an example of the support tape of FIG. 1 applied to the ankle.

FIG. 3 illustrates application of the support tape 100 to the anterior section of the lower leg and ankle 210. In this configuration, the support tape 100 may provide support to the tibialis anterior tendon that may treat tibialis anterior tendonitis for example. As shown in FIG. 3, the first portion 104 of the body 102 of the support tape 100 may attach to the lower anterior section of the shin, extend over the ankle, and conclude on the medial side of the plantar aspect of the foot. Additionally, the wings 110, 112 of the support tape 100 may be stretched to cover a portion of the medial malleolus and extend distally over the lateral malleolus. In such configuration, the support tape 100 may be configured to provide rigidity from the anterior shin through the ankle and may provide treatment for anterior tibial tendonitis.

In a similar treatment, the support tape 100 may be applied to the posterior and medial section of the lower leg and ankle. In this configuration, the support tape 100 may provide support to the tibialis posterior tendon that may treat tibialis posterior tendonitis. The first portion 104 of the body 102 of the support tape 100 may attach to the lower, medial, posterior section of the lower leg, extend over the medial malleolus, and conclude on the plantar aspect of the foot, on the medial side. Additionally, the wings 110, 112 of the support tape 100 may be stretched to cover the calcaneus and the anterior portion of the ankle. In such a configuration, the support tape 100 may be configured to provide rigidity from the posterior and medial portion of the lower leg through the ankle and may provide treatment for posterior tibial tendonitis.

Figure 4:
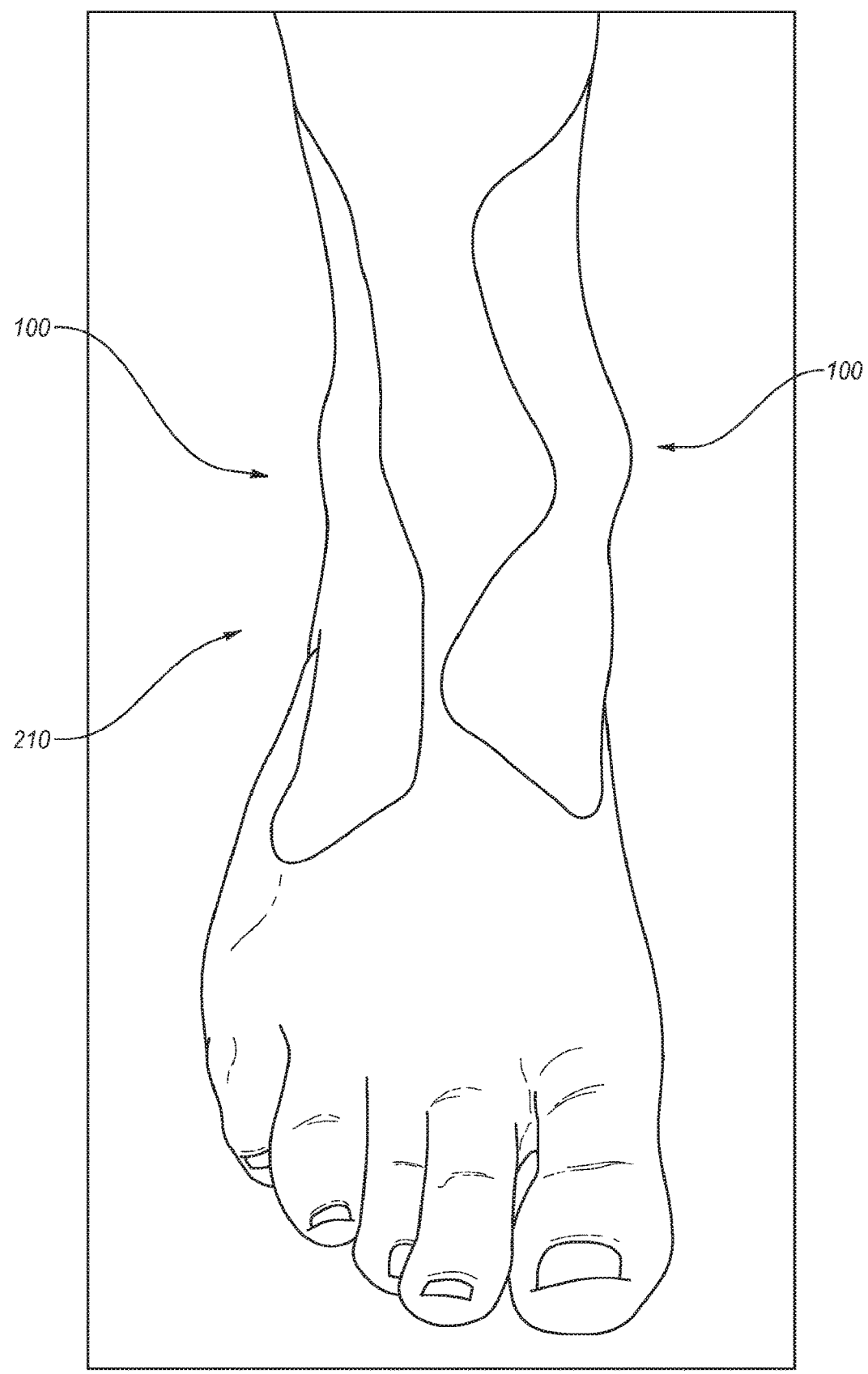
FIG. 4 illustrates an example of the support tape of FIG. 1 applied to opposite sides of the ankle.

FIG. 4 illustrates application of a support tape 100 to the medial portion of the ankle and a support tape 100 to the lateral portion of the ankle, although forms where a single support tape 100 is applied to only one of the medial and lateral portions of the ankle are possible. In this configuration, the support tapes 100 may provide support to the ankle, may provide the ankle with greater stability, and may reduce pain associated with ligament damage. One of the support tapes 100 may be applied to cover the medial portion of the ankle, where one end may be attached to the medial portion of the tibial side of the lower leg, may cover the medial malleolus, and the other end of the support tape 100 may be attached to the plantar aspect of the foot, distally located relative to the calcaneus. One of the wings 110, 112 of the first support tape 100 may be stretched across the Achilles tendon, above the calcaneus, and the other of the wings 110, 112 may be stretched in the opposite direction, across the medial portion of the top of the foot, which may be above the arch of the foot.

A second support tape 100 may also be applied to the ankle area. In this configuration, one end of the second support tape 100 may be attached to the lateral portion of the fibular side of the lower leg, may cover the lateral malleolus, and the other end of the support tape 100 may be attached to the plantar aspect of the foot, distally located relative to the calcaneus. One of the wings 110, 112 of the second support tape 100 may be stretched across the Achilles tendon, above the calcaneus, and the other of the wings 110, 112 may be stretched in the opposite direction, across the lateral portion of the top of the foot.

Figure 5:
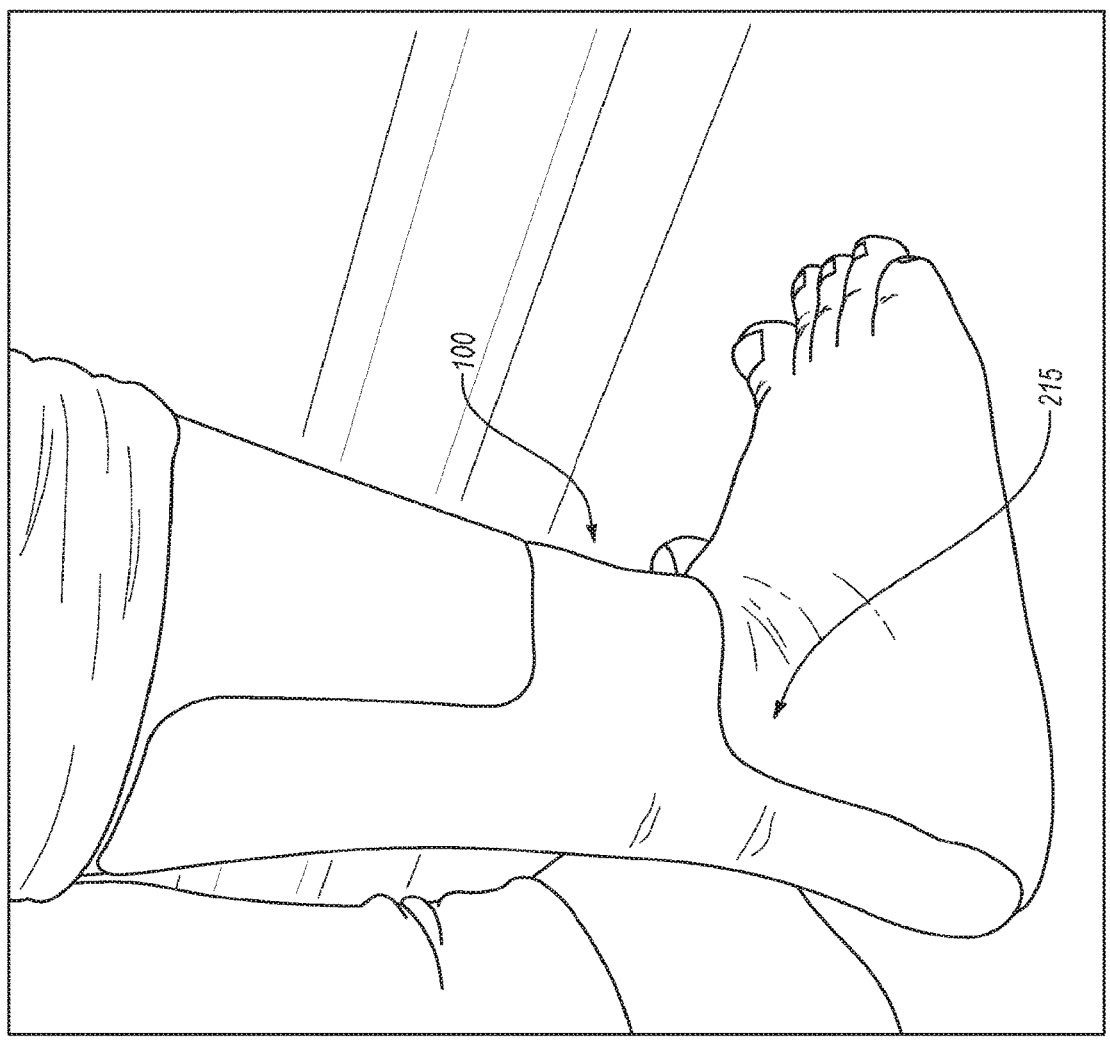
FIG. 5 illustrates an example of the support tape of FIG. 1 applied to the Achilles tendon.

FIG. 5 illustrates application of the support tape 100 applied to the Achilles tendon 215. In this configuration, the support tape 100 may provide support to the Achilles tendon that may provide treatment for Achilles tendonitis, for example. As shown in FIG. 5, the first portion 104 of the body 102 of the support tape 100 may attach to the lower posterior section of the lower leg, extend over the Achilles tendon, and conclude on the calcaneus. Additionally, the wings 110, 112 of the support tape 100 may wrap around the ankle, with one of the wings 110, 112 covering the medial malleolus, and the other of the wings 110, 112 covering the lateral malleolus. In alternative embodiments, the wings 110, 112 may be configured to be located above the malleolus, or below the malleolus. In all such configurations, the support tape 100 may be configured to provide rigidity along the Achilles tendon and may provide treatment for Achilles tendonitis.

Figure 6:
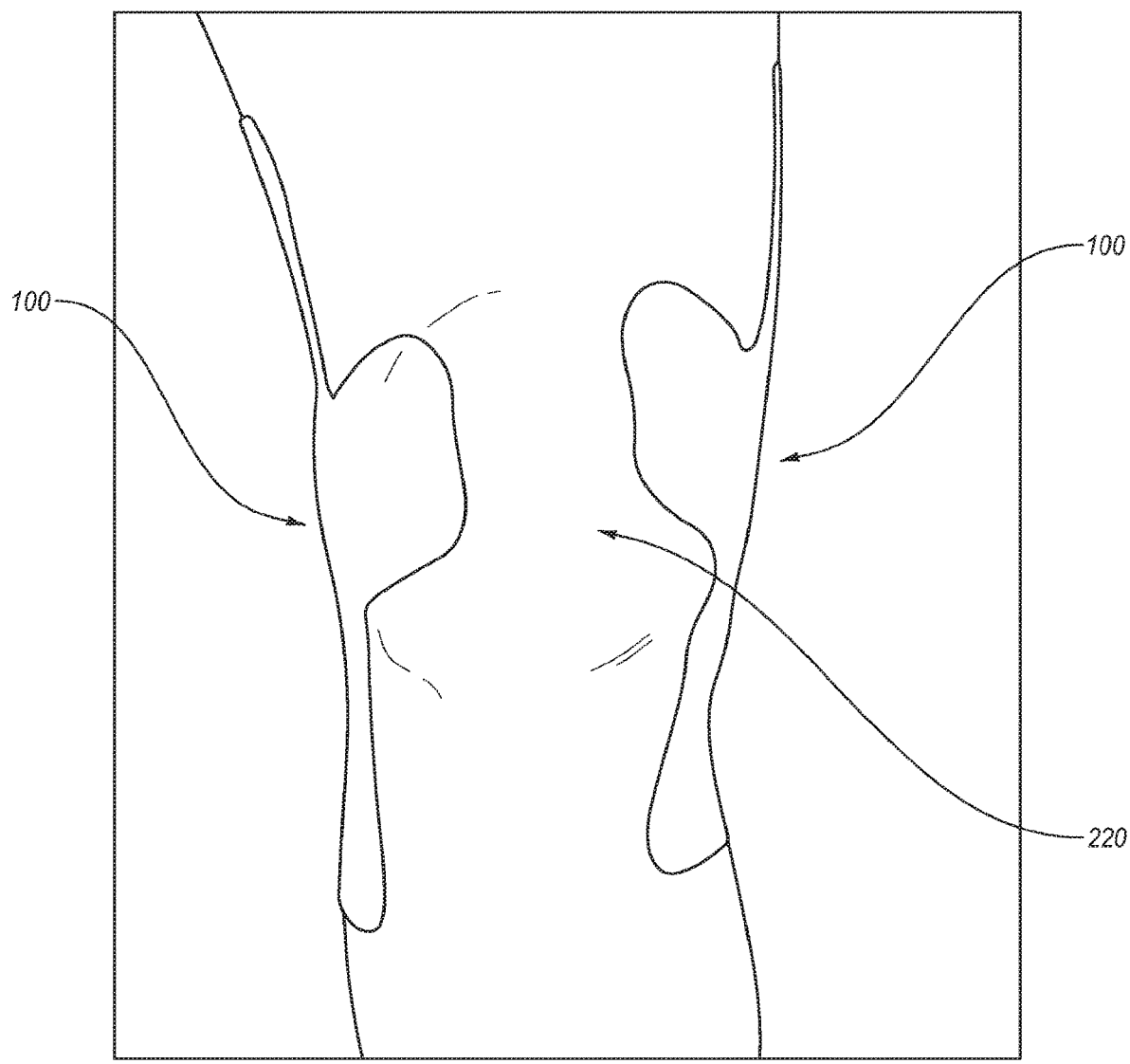
FIG. 6 illustrates an example of the support tape of FIG. 1 applied to opposite sides of the knee.

FIG. 6 illustrates application of a support tape 100 applied medially to the knee 220 and a support tape 100 applied laterally to the knee 220. Forms where a single support tape 100 is applied laterally or medially to the know are also possible. In this configuration, the two support tapes 100 may provide support to the knee, may provide the knee with greater stability, and may reduce pain located in the knee area. As shown in FIG. 6, the first portion 104 of the body 102 of a first support tape 100 may be applied to the medial portion of the quadriceps, above the knee, may extend inferiorly past the medial knee joint, and may continue down to the upper, medial portion of the lower leg. Additionally, the wings 110, 112 of the first support tape 100 may be stretched to cover the patella in one direction and the popliteal fossa in the opposite direction.

A second support tape 100 may also be applied to the knee area, as shown in FIG. 6, which may be applied to the lateral portion of the knee. In this configuration, the first portion 104 of the body 102 of the second support tape 100 may be applied to the lateral portion of the quadriceps, above the knee, may extend inferiorly past the lateral knee joint, and may continue down to the upper, lateral portion of the lower leg. Additionally, the wings 110, 112 of the second support tape 100 may be stretched to cover the patella in one direction and the popliteal fossa in the opposite direction.

Figure 7:
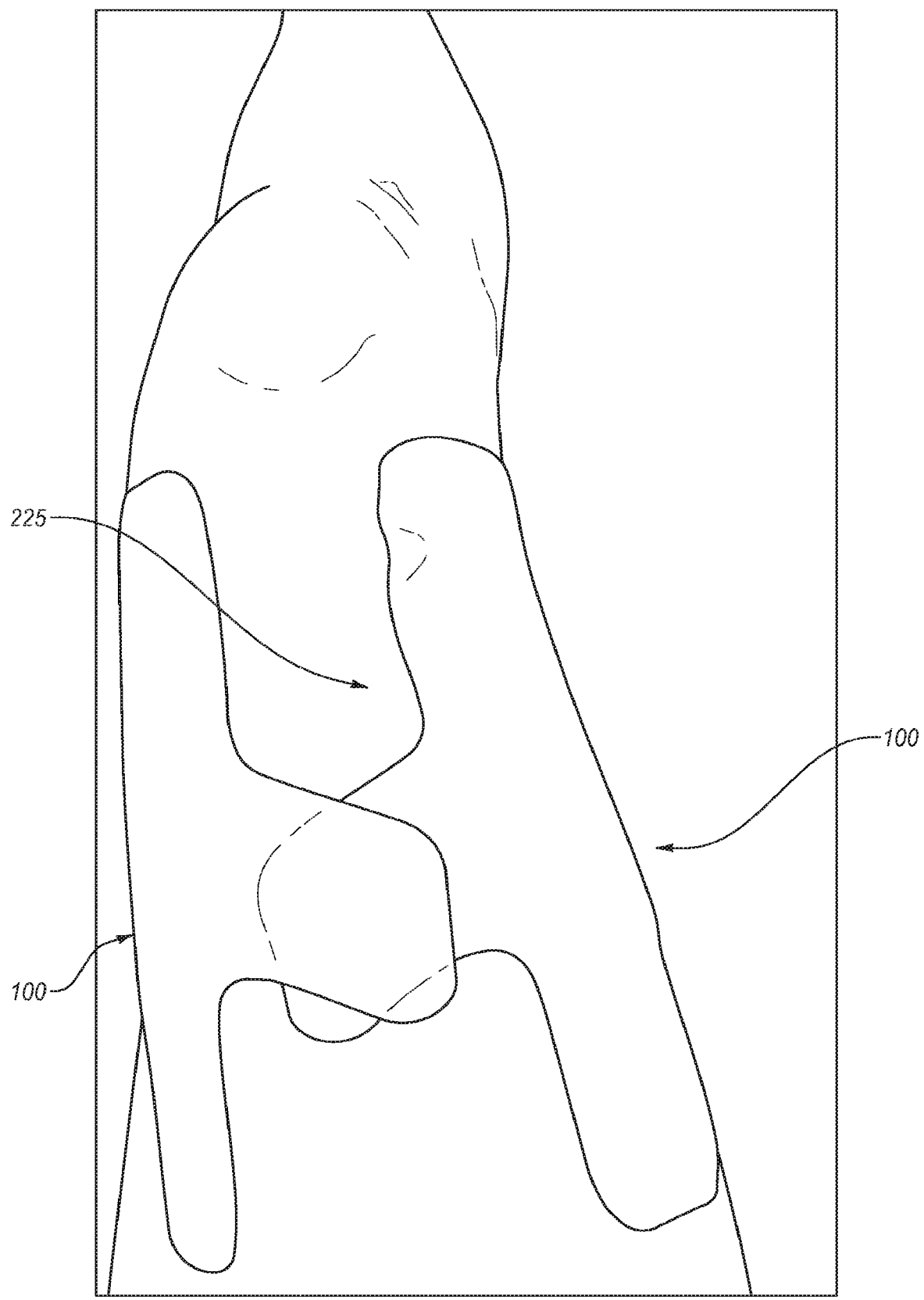
FIG. 7 illustrates an example of the support tape of FIG. 1 applied medially and laterally to the quadriceps.

FIG. 7 illustrates an embodiment of two support tapes 100 applied medially and laterally to the quadriceps 225. In this configuration, the two support tapes 100 may provide support to the quadriceps and may help treat strains to the quadricep muscles. As shown in FIG. 7, the first portion 104 of the body 102 of a first support tape 100 may be applied to the medial portion of the quadriceps, superior to the knee, and may extend up the medial side of the quadriceps. The wings 110, 112 of the first support tape 100 may wrap around the upper leg, such that one of the wings 110, 112 attaches to the anterior portion of the quadriceps and the other of the wings 110, 112 attaches in the opposite direction, to the posterior portion of the quadriceps.

Also shown in FIG. 7 is a second support tape 100 that may be applied to the lateral portion of the quadriceps 225. The second support tape 100 may be applied to the lateral portion of the quadriceps, superior to the knee, and may extend up the lateral side of the quadriceps. The wings 110, 112 of the second support tape 100 may wrap around the upper leg, such that one of the wings 110, 112 attaches to the anterior portion of the quadriceps and the other of the wings 110, 112 attaches in the opposite direction, to the posterior portion of the quadriceps.

When combined as shown in FIG. 7, the first support tape 100 and the second support tape 100 may provide support to the quadriceps and may help treat strains to the quadricep muscles. In alternative embodiments, the wings 110, 112 of the two support tapes 100 may overlap on the anterior portion of the quadriceps, may overlap on the posterior portion of the quadriceps, may overlap on both the anterior and posterior portion of the quadriceps, or may not overlap in any configuration.

Opposite of what is illustrated in FIG. 7, a support tape 100 may also be applied to the posterior portion of the upper leg, specifically to the hamstring. In this configuration, the support tape 100 may provide support to the hamstring muscle that may provide treatment for strains to the hamstring. In one form, the first portion 104 of the body 102 of the support tape 100 may be applied to the posterior portion of the upper leg, superior to the popliteal fossa, and may extend up the posterior portion of the leg to cover some or all of the hamstring. Additionally, the wings 110, 112 may extend in opposite directions, to wrap the upper leg, such that one of the wings 110, 112 attaches to the medial quadricep area and the other of the wings 110, 112 attaches to the lateral quadricep area.

Figure 8:
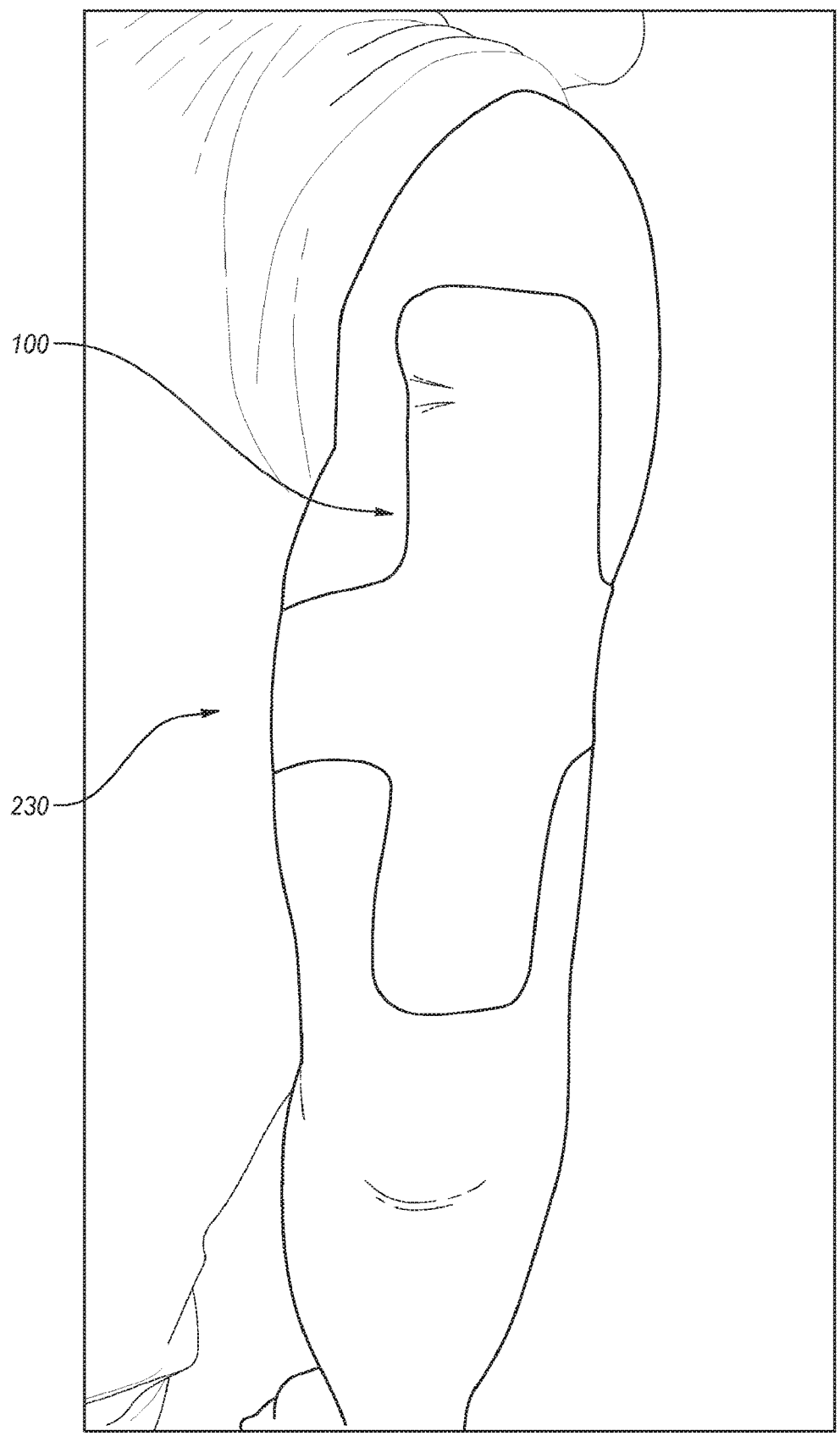
FIG. 8 illustrates an example of the support tape of FIG. 1 applied to the triceps.

FIG. 8 illustrates application of the support tape 100 applied to the posterior and lateral portion of the upper arm, specifically to the triceps 230. In this configuration, the support tape 100 may provide support to the triceps muscle that may provide treatment for strains to the triceps. As shown in FIG. 8, the first portion 104 of the body 102 of the support tape 100 may be applied to the posterior portion of the upper arm, on or inferior to the deltoid, may extend down the posterior portion of the upper arm, along the triceps, and may conclude at the elbow, or superior thereto. The first portion 104 of the body 102 of the support tape 100 may cover some or all of the triceps muscle when applied. Additionally, the wings 110, 112 may extend in opposite directions, to wrap the upper arm, such that one of the wings 110, 112 attaches to the posterior triceps area and one of the wings 110, 112 attaches across the biceps area.

Figure 9:
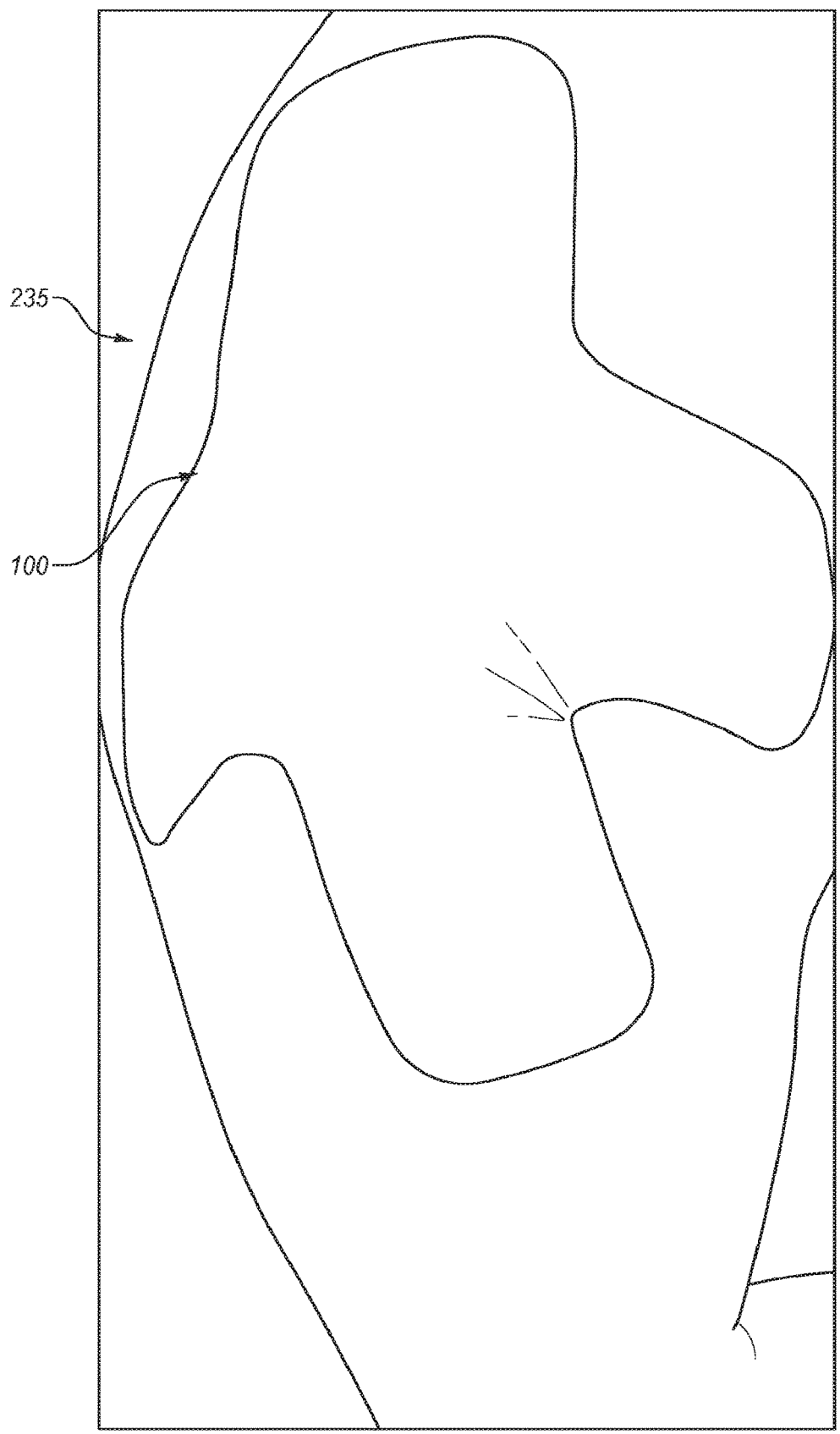
FIG. 9 illustrates an example of the support tape of FIG. 1 applied to the deltoid.

FIG. 9 illustrates application of the support tape 100 to the shoulder area, specifically to the deltoid 235. In this configuration, the support tape 100 may provide support to the deltoid muscle that may provide treatment for strains to the deltoid. As shown in FIG. 9, the first portion 104 of the body 102 of the support tape 100 may be applied to the upper portion of the shoulder, above the clavicle and the scapula for example, and may extend down the lateral deltoid, until the support tape 100 nears the insertion point of the deltoid. The first portion 104 of the support tape 100 may cover some or all of the deltoid muscle when applied. Additionally, the wings 110, 112 may extend in opposite directions, to wrap the shoulder, such that one of the wings 110, 112 attaches to the anterior deltoid area and the other of the wings 110, 112 attaches to the posterior deltoid area.

The support tape 100 may also be used at other anatomical locations on the upper portion of the body. For example, in one form, the support tape 100 may be applied to the back area, specifically to the lower trapezius. In this configuration, the support tape 100 may provide support to the trapezius muscle that may provide treatment for strains to the upper back and trapezius muscle. In one aspect, the first portion 104 of the body 102 of the support tape 100 may be applied to the posterior deltoid, and may extend diagonally down the upper back, until the support tape 100 nears the origin point of the lower trapezius on the spine. The first portion 104 of the support tape 100 may cover some or all of the rhomboid major and may cover some or all of the shoulder and/or clavicle when applied. Additionally, the wings 110, 112 may extend in opposite directions, such that one of the wings 110, 112 attaches to a superior portion of the trapezius, compared to an end of the first portion 104, also near the spine, and one of the wings 110. 112 attaches to the latissimus dorsi area, inferior to the teres major.

In another form, the support tape 100 may be applied to the neck and back area, specifically to the upper trapezius. In this configuration, the support tape 100 may provide support to the trapezius muscle that may provide treatment for strains to the upper back and neck as well as the trapezius muscle. In one aspect, the first portion 104 of the body 102 of the support tape 100 may be applied to a lateral position on the neck, and may extend down the upper back as far as the support tape 100 will reach, while covering the trapezius muscle. Additionally, the wings 110, 112 may extend in opposite directions, such that one of the wings 110, 112 attaches to a superior portion of the trapezius near the spine, and another wing 110, 112 wraps across the clavicle, in a general direction toward the pectoral muscle.

In yet another form, the support tape 100 may be applied to the neck area, specifically along the back of the neck and down the spine. In this configuration, the support tape 100 may provide support to the upper trapezius muscle that may provide treatment for strains to neck as well as the upper trapezius muscle. In one aspect, the first portion 104 of the body 102 of the support tape 100 may be applied to a posterior position on the neck and may extend down the spinal column as far as the support tape 100 will reach, continually covering the spine. Additionally, the wings 110, 112 may extend in opposite directions, superiorly and laterally from the center of the first portion 104, such that both wings 110, 112 extend in such direction as to reach across a medial portion of the clavicle.

In all embodiments, the specific location of the support tape 100 may be modified to provide support as needed, and as determined by a practitioner with knowledge in the art.

In one embodiment, an anatomical support device includes an elongate body including a first portion extending along a longitudinal axis between a first end and an oppositely positioned second end, a first wing extending transversely from the first portion, and a second wing extending transversely from the first portion. An adhesive material is positioned on at least a portion of one side of the elongate body. The elongate body is rigid in a first direction extending in-line with the longitudinal axis and is stretchable in a second direction extending transversely to the longitudinal axis.

In one form, the device also includes a backing material applied to and covering the adhesive material. In one aspect, the backing material includes a plurality of cooperating pieces configured to cover the adhesive material. In another aspect, one or more of the cooperating pieces of the backing material overlap with one another. In another aspect, a plurality of perforations is positioned between the cooperating pieces of the backing material, the perforations configured to facilitate individual removal of the cooperating pieces from the adhesive material.

In one form, the first portion includes a first width adjacent to the first end and a second width adjacent to the second end, the second width being less than the first width. In one form, an outer periphery of the elongate body includes a plurality of arcuate corners. In one aspect, a number of the plurality of arcuate corners includes a concave configuration and a number of the plurality of arcuate corners includes a convex configuration.

In one form, the first wing extends along a first axis extending transversely to the longitudinal axis and the second wing extends along a second axis extending transversely to the longitudinal axis. In one aspect, the first axis and the second axis extend obliquely to the longitudinal axis.

In one form, the first portion of the elongate body includes a first number of removable sections positioned adjacent to the first end, the first number of removable sections configured to facilitate adjustment of a distance between the first end and the second end. In one aspect, the first portion of the elongate body includes a second number of removable sections positioned adjacent to the second end, the second number of removable sections configured to facilitate adjustment of a distance between the first end and the second end.

In another embodiment, a method for treating plantar fasciitis includes providing an anatomical support device. The anatomical support device includes an elongate body including a first portion extending along a longitudinal axis between a first end and an oppositely positioned second end, a first wing extending transversely from the first portion, and a second wing extending transversely from the first portion. An adhesive material is positioned on at least a portion of one side of the elongate body. The elongate body is rigid in a first direction extending in-line with the longitudinal axis and is stretchable in a second direction extending transversely to the longitudinal axis. The method also includes applying the device to the bottom of a human foot including a number of toes, a heel, a malleolus, and an extensor retinaculum. The first end is positioned toward the toes, the second end is positioned toward the heel, the first wing is stretched in a direction of the malleolus, and the second wing is stretched in a direction of the extensor retinaculum.

In one form, the method also includes successively removing a number of cooperating pieces of a backing material applied to and covering the adhesive material.

In one form, an outer periphery of the elongate body of the device includes a plurality of arcuate corners. In one aspect, a number of the plurality of arcuate corners includes a concave configuration and a number of the plurality of arcuate corners includes a convex configuration.

In one form, the first wing extends along a first axis extending transversely to the longitudinal axis and the second wing extends along a second axis extending transversely to the longitudinal axis. In one aspect, the first axis and the second axis extend obliquely to the longitudinal axis.

In one form, the first portion of the elongate body includes a number of removable sections positioned adjacent to the first end, the removable sections being configured to facilitate adjustment of a distance between the first end and the second end. In one aspect, the first portion of the elongate body includes a second number of removable sections positioned adjacent to the second end, the second number of removable sections being configured to facilitate adjustment of a distance between the first end and the second end.

With respect to the use of substantially any plural or singular terms herein, translating from the plural to the singular or from the singular to the plural may be performed as is appropriate to the context or application. The various singular/plural permutations may be expressly set forth herein for sake of clarity. A reference to an element in the singular is not intended to mean "one and only one" unless specifically stated, but rather "one or more." Moreover, nothing disclosed herein is intended to be dedicated to the public regardless of whether such disclosure is explicitly recited in the above description.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Furthermore, in those instances where a convention analogous to "one or more of A, B, and C", "at least one of A, B, and C", "one or more of A, B, or C" "at least one of A, B, or C, etc." is used, in general, such a construction is intended to generally have a disjunctive interpretation (e.g., "a system having at least one of A, B, or C" or "a system having at least one of A, B, and C" would include but not be limited to systems that include A alone, B alone, C alone, A and B together, A and C together, B and C together, or A, B, and C together, etc.). Also, a phrase presenting two or more alternative terms, whether in the description, claims, or drawings, should be understood to include one of the terms, either of the terms, or both terms. For example, the phrase "A or B" will be understood to include the possibilities of "A" or "B" or "A and B." This interpretation of the phrase "A or B" is still applicable even though the term "A and/or B" may be used at times to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
   obtaining an anatomical support device comprising
      a material having a first end, a second end positioned opposite the first end, and a first portion extending along a longitudinal axis between the first end and the second end,
      the material further having a first wing extending along a first axis away from the first portion and a second wing extending along a second axis away from the first portion, wherein the first axis and the second axis each intersect the longitudinal axis at an angle in a range from about 60 degrees to about 80 degrees,
      the material being substantially inextensible along the longitudinal axis from the first end to the second end and elastically extensible along a lateral axis extending orthogonally with respect to the longitudinal axis, and
      an adhesive positioned on at least a portion of one side of the material,
   applying the anatomical support device to a bottom of a foot of a patient such that the first end covers a ball of the foot and the second end extends to a heel of the foot;

securing, by the adhesive after the applying, the anatomical support device to the bottom of the foot; and providing, by the material after the applying and securing, substantially inelastic support of plantar fascia of the foot along the longitudinal axis and elastic support of a medial arch of the foot.

2. The method of claim 1, wherein the material is a woven material.

3. The method of claim 1, wherein the applying comprises wrapping the first wing partially around the foot so that a distal end of the first wing terminates proximate an anterior aspect of a medial malleolus of the foot.

4. The method of claim 1, wherein the applying comprises wrapping the first wing partially around the foot so that a distal end of the first wing overlays an apical insertion of a flexor retinaculum of the foot.

5. A method of treating a patient suffering from plantar fasciitis, the method comprising:
obtaining an anatomical support device comprising
an elongate body including a first portion extending along a longitudinal axis between a first end and a second end positioned opposite the first end, a first wing extending along a first axis away from the first portion, and a second wing extending along a second axis away from the first portion, wherein the first axis and the second axis each intersect the longitudinal axis at an angle in a range from about 60 degrees to about 80 degrees, and
the elongate body being formed of material that is substantially inextensible along the longitudinal axis from the first end to the second end and is elastically extensible along a lateral axis extending orthogonally with respect to the longitudinal axis; and
adhering the anatomical support device to a bottom of a foot of the patient such that the first end covers a ball of the foot and the second end extends to a heel of the foot.

6. The method of claim 5, wherein the first axis and the second axis each intersect the longitudinal axis at an angle in a range from about 65 degrees to about 75 degrees.

7. The method of claim 6, wherein the first axis and the second axis each intersect the longitudinal axis at an angle of about 70 degrees.

8. The method of claim 5, wherein the material is a woven material.

9. A method comprising:
obtaining an anatomical support device comprising
an elongate body including a first portion extending along a longitudinal axis between a first end and a second end positioned opposite the first end, a first wing extending along a first axis away from the first portion, and a second wing extending along a second axis away from the first portion, wherein the first axis and the second axis each intersect the longitudinal axis at an angle in a range from about 60 degrees to about 80 degrees,
the elongate body being formed of material that is substantially inextensible along the longitudinal axis and elastically extensible along a lateral axis extending orthogonally with respect to the longitudinal axis, and
an adhesive material positioned on at least a portion of one side of the elongate body;
applying the anatomical support device to a bottom of a foot of a person such that (1) the longitudinal axis is aligned with a length of the foot, (2) the lateral axis is aligned with a width of the foot, and (3) the first wing wraps partially around the foot and terminates at an anterior aspect of a medial malleolus of the foot so as to overlay an apical insertion of a flexor retinaculum of the foot; and
securing, by the adhesive material after the applying, the anatomical support device to the bottom of the foot.

10. The method of claim 9, wherein the material is a woven material.

* * * * *